United States Patent [19]

Besson et al.

[11] Patent Number: 4,855,513

[45] Date of Patent: Aug. 8, 1989

[54] CHLORINATION OF PHENOLIC COMPOUNDS

[75] Inventors: Bernard Besson, Pont de Claix; Jean-Roger Desmurs, Saint-Symphorien D'Ozon; Isabelle Jouve, Villeurbanne, all of France

[73] Assignee: Rhone-Poulenc Chimie, Courbevoie, France

[21] Appl. No.: 165,007

[22] Filed: Mar. 7, 1988

[30] Foreign Application Priority Data

Mar. 5, 1987 [FR] France ................................ 87 03208

[51] Int. Cl.$^4$ ........................ C07C 37/62; C07C 39/32
[52] U.S. Cl. .................................... 568/779; 568/765; 568/774; 568/776
[58] Field of Search ................ 568/774, 776, 779, 765

[56] References Cited

U.S. PATENT DOCUMENTS

| | | | |
|---|---|---|---|
| 2,440,602 | 4/1948 | Foster et al. | 568/779 |
| 2,494,993 | 1/1950 | Foster | 568/779 |
| 4,237,321 | 12/1980 | Cuthbertson | 568/776 |

FOREIGN PATENT DOCUMENTS

| | | | |
|---|---|---|---|
| 0002373 | 6/1979 | European Pat. Off. | 568/779 |
| 216714 | 4/1987 | European Pat. Off. | 568/776 |
| 2212333 | 9/1987 | Japan | 568/776 |
| 2258332 | 11/1987 | Japan | 568/776 |
| 639054 | 10/1983 | Switzerland | 568/776 |
| 573477 | 11/1945 | United Kingdom | 568/779 |
| 2044246 | 10/1980 | United Kingdom | 568/776 |
| 2177396A | 1/1987 | United Kingdom | 568/779 |

*Primary Examiner*—Werren B. Lone
*Attorney, Agent, or Firm*—Burns, Doane, Swecker & Mathis

[57] ABSTRACT

The chlorophenols, e.g., 2,4,6-trichlorophenol, are efficiently prepared by chlorinating an ortho-/para-substituted phenolic compound with gaseous chlorine, whether in molten state or in a solvent reaction medium, in the presence of a catalytically effective amount of a primary, secondary or tertiary amine.

18 Claims, No Drawings

CHLORINATION OF PHENOLIC COMPOUNDS

CROSS-REFERENCE TO COMPANION APPLICATIONS

Copending applications, Ser. No. 164,894 and Ser. No. 164,966, both filed concurrently herewith and both assigned to the assignee hereof.

BACKGROUND OF THE INVENTION

1. Field of the Invention

The present invention relates to the chlorination of phenolic compounds with gaseous chlorine, and more especially, to such chlorination of ortho-substituted phenols.

2. Description of the Prior Art 2,4,6-Trichlorophenol is an important phenolic compound which can be prepared by the chlorination of a phenolic compound substituted at the ortho positions.

The usual process for preparing 2,4,6-trichlorophenol consists of the chlorination of 2,4-dichlorophenol.

However, a small proportion of 2,4,5-trichlorophenol is concomitantly formed (on the order of 0.003 to 0.010% of the weight of 2,4,6-trichlorophenol). 2,4,6-Trichlorophenol, an intermediate for the synthesis of other valuable compounds, must not contain trace amounts of this undesirable isomer.

One solution to this problem would be to chlorinate 2,6-dichlorophenol, which would completely avoid the formation of 2,4,5-trichlorophenol. 2,3,6-Trichlorophenol, likely to be formed in this case in trace amounts, is much less troublesome than 2,4,5-trichlorophenol.

Nonetheless, when 2,6-dichlorophenol is indeed chlorinated with gaseous chlorine, it is found that adequate yields are not obtained. In particular, a large amount of 2,4,5,6,6-pentachloro-2-cyclohexenone is formed, which makes the reaction mixture very unstable and quite difficult to purity.

SUMMARY OF THE INVENTION

Accordingly, a major object of the present invention is the provision of an improved process for the chlorination, in good yields, of both the ortho- and para-substituted phenols, which improved process conspicuously avoids those disadvantages and drawbacks to date characterizing the state of this art.

Briefly, the present invention features the chlorination, with gaseous chlorine, of phenolic compounds having the general formula (I):

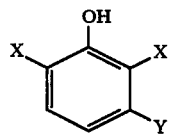

(I)

in which the symbols X, which may be identical or different, are each a chlorine atom, a bromine atom, a methyl or ethyl group, a methoxy or ethoxy group, an acetoxy group, an $NO_2$ group, or an acylamino group having 1 to 4 carbon atoms; and the symbol Y is a hydrogen atom, a methyl or ethyl group; or a methoxy or ethoxy group, by carrying out the reaction in the presence of a catalytically effective amount of at least one primary, secondary or tertiary amine.

DETAILED DESCRIPTION OF THE PREFERRED EMBODIMENTS OF THE INVENTION

More particularly according to the present invention, by the term "amine" is intended any organic nitrogen compound, liquid or solid under the working conditions of the process, containing one or more amine groups.

Such a compound can also contain one or more other functional groups such as, for example, the hydroxyl group, the carboxylic acid group, the carboxylic acid ester group, the amide group or the imine group.

It will of course be appreciated that the amines used can also be introduced in the form of their salts, and more especially of their respective hydrochlorides.

By the term "amine" is also intended ammonia, as well as the salts, in particular the amine hydrochlorides.

The process of the invention may be carried out in the absence of solvent: the reactants are then in the molten state. This embodiment of the invention generally provide the best results.

It is also possible to conduct the reaction in a liquid medium of, in particular, an aliphatic ether, an aliphatic hydrocarbon, a chlorinated aliphatic hydrocarbon, a chlorobenzene or a bromobenzene.

Representative aliphatic ethers are dipropyl ether, diisopropyl ether and methyl tert-butyl ether.

Representative aliphatic hydrocarbons are hexane, heptane, octane, nonane and decane.

Exemplary chlorinated hydrocarbons are perchlorinated hydrocarbons such as, in particular, carbon tetrachloride, tetrachloroethylene, hexachloroethane, hexachloropropene and hexachlorobutadiene; and partially chlorinated hydrocarbons such as methylene chloride, dichloroethane, tetrachloroethane, trichloroethylene, 1-chlorobutane and 1,2-dichlorobutane.

Exemplary chlorobenzenes are monochlorobenzene, 1,2-dichlorobenzene, 1,3-dichlorobenzene, 1,4-dichlorobenzene, and especially mixtures of the different chlorobenzenes. Exemplary bromobenzenes are monobromobenzene or mixtures of monobromobenzene with one or more dibromobenzenes.

When the process of the invention is carried out in a solvent medium, the concentration of the chlorophenol of the formula (I) in the solvent is not critical. It will depend, in particular, on the solubility of the chlorophenol in the solvent used.

The amines which serve as a catalyst in the subject process are more preferably the amines having the general formula (II):

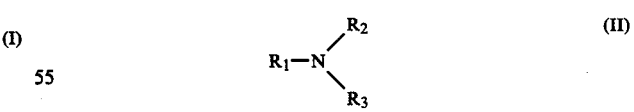

(II)

in which $R_1$, $R_2$ and $R_3$, which may be identical or different, are each a linear alkyl radical having from 1 to 12 carbon atoms, a secondary alkyl radical having from 3 to 12 carbon atoms or a tertiary alkyl radical having from 4 to 12 carbon atoms, with the proviso that such alkyl radicals may contain one or two —O—ether groups or hydroxyl, amine, carboxylic acid, carboxylic acid ester, amide or imine groups; a phenyl radical, a cyclohexyl radical, a cycloheptyl radical or a cyclopentyl radical; a phenylalkyl, cyclohexylalkyl, cycloheptylalkyl or cyclopentylalkyl radical, the alkyl moiety of which contains from 1 to 4 carbon atoms; or a hydrogen atom; with the further provisos that:

$R_1$ may be an $NH_2$ group;

$R_2$ and $R_3$ may from, together with the nitrogen atom from which they depend, a saturated heterocycle or a heterocycle containing one or more double bonds, optionally substituted with one or more alkyl groups from having 1 to 4 carbon atoms;

$R_2$ and $R_3$ or $R_1$, $R_2$ and $R_3$ may form, together with the nitrogen atom from which they depend and with one or more other nitrogen and/or oxygen and/or sulfur atoms, a saturated or unsaturated heterocycle optionally substituted with one or more alkyl groups having from 1 to 4 carbon atoms;

$R_1$, $R_2$ and $R_3$ may form, together and with the nitrogen atom from which they depend, an unsaturated heterocycle optionally substituted with one or two methyl or ethyl groups;

$R_2$ and $R_3$ or $R_1$, $R_2$ and $R_3$ may form, together with the nitrogen atom from which they depend and optionally with one or more other nitrogen and/or oxygen and/or sulfur atoms, a saturated or unsaturated polycyclic compound optionally substituted with one or more alkyl groups having 1 to 4 carbon atoms.

Exemplary of such amines of formula (II), the following are representative:

(i) ammonia;

(ii) primary amines such as n-propylamine, isopropylamine, isobutylamine, n-butylamine, tert-butylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, glycine ether ester, ethanolamine, ethylenediamine, hexamethylenediamine, N-aminoethylpyrrolidine, pyrazoline, lysine, n-aminomorpholine and N-aminopiperidine;

(iii) secondary amines such as dibutylamine, dipropylamine, methylpropylamine, methylbutylamine, methylisobutylamine, methyl-tert-butylamine, methylbenzylamine, di-tert-butylamine, 1-methylcyclopentylamine, 1-methylcyclohexylamine, dicyclohexylamine, morpholine, imidazole, pyrrolidine, imidazolidine, piperazine and indole;

(iv) tertiary amines such as triethylamine, tributylamine, pyridine, tris(3,6-dioxaheptyl) amine and 1,8-diazabicyclo[5.4.0]undec-7-ene.

It is also possible to use amino compounds such as hydrazine or its derivatives, in particular the derivatives obtained by substitution of one or two hydrogen atoms with alkyl, aryl, cycloaliphatic or heterocyclic radicals.

The quantity of the amine used in the process can vary over very wide limits.

It usually represents from 0.005% to 25% by weight relative to the weight of the phenolic compound. Preferably, from 0.015% to 5% by weight of amine relative to the phenolic compound will be employed, in order to have sufficient efficacy, while not having an excessive amount of the amine.

Among the amines of the general formula (II), more preferred are the primary or secondary amines of the formula (III):

in which $R_2$ or $R_3$ may be a hydrogen atom; and $R_2$ and $R_3$, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical; with the provisos that:

$R_2$ and $R_3$ may form, together with the nitrogen atom from which they depend and with another nitrogen and/or oxygen atom, a saturated heterocycle or a heterocycle containing one or more unsaturated bonds; and $R_2$ and/or $R_3$ may contain one or more amine, hydroxyl or carboxylic acid ester groups.

As specific examples of primary amines of the general formula (III), representative are n-propylamine, isopropylamine, n-butylamine, isobutylamine, tert-butylamine, n-pentylamine, 2-methylpentylamine, 3-methylpentylamine, 2-ethylhexylamine, laurylamine, cyclohexylamine, cyclopentylamine, benzylamine, glycine ethyl ester and ethanolamine.

As regards, more especially, the secondary amines of general formula (III), more preferred are those in which at least one of the symbols $R_2$ and $R_3$, and preferably both symbols $R_2$ and $R_3$, are a secondary alkyl radical having from 3 to 10 carbon atoms, such as isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl and 5-decyl; a cyclohexyl or cyclopentyl radical; and those in which $R_2$ and $R_3$ form, together with the nitrogen atom from which they depend, a heterocycle optionally containing another nitrogen atom or an oxygen atom.

As specific examples of such secondary amines, diisopropylamine, diisobutylamine, dicyclohexlamine, morpholine and imidazole are representative.

The quantity of chlorine used in the process of the invention depends essentially on the desired degree of conversion of the phenolic compound (I).

In practice, most frequently the chlorine is introduced by bubbling it into the reaction medium. The pressure in the apparatus is hence substantially equal to or slightly greater than atmospheric pressure.

The chlorine can be used either alone or it can be diluted with an inert gas such as nitrogen, for example. The presence of an inert gas enables, if necessary, the flow rate of the gas to be increased without a concomitant increase in the quantity of chlorine introduced over a given period of time.

The gaseous chlorine used in the present process can also be formed in situ, from hydrochloric acid, by adding an oxidizing compound such as, for example, hydrogen peroxide.

The temperature at which the process of the invention is carried out is generally below or equal to 180° C. The lower limit is not critical. It is conditioned on the necessity to have a liquid reaction mixture.

When the reaction is carried out in the molten state, this lower temperature will hence vary according to the phenolic compound (I) being subjected to the chlorination. Thus, when 2,6-dichlorophenol is chlorinated, a temperature of at least 65° C. is required.

When the reaction is carried out in a solvent medium, it is possible to lower the temperature to 20° C., for example.

Preferably, however, the temperature will range from 40° C. to 120° C. if the reaction is conducted in a solvent medium.

If the reaction is carried out in a molten state, the preferred temperatures will range from 40° to 120° C., except, of course, for phenolic compounds having a melting point above 40° C., for which the preferred temperature range will range from their melting point to 120° C.

Especially suitable phenolic compounds of the formula (I) to be chlorinated are 2,6-dichlorophenol, 2,6-dimethoxyphenol, 2-chloro-6-methoxyphenol, 2-chloro-6-methylphenol, 2,6-dichloro-3-methylphenol, 2,6-dichloro-3-methoxyphenol, 2-bromo-6-methoxyphenol, 2-chloro-6-nitrophenol and 2-chloro-6-acetamidophenol.

It is possible, if so desired, to chlorinate mixtures of these phenolic compounds.

The process of the invention is most especially suitable for the chlorination of 2,6-dichlorophenol into 2,4,6-trichlorophenol, since it enables the latter compound to be obtained while essentially avoiding the formation of undesirable byproducts such as 2,4,5,6,6-pentachloro-2-cyclohexanone, i.e., byproduction of such compounds to an extent of less than 3% by weight.

When the process of the invention is applied to 2,6-dichlorophenol, the latter may itself be produced, in particular, by the chlorination of 2-chlorophenol using gaseous chlorine, in the presence of a primary, secondary or tertiary amine as described above.

It is thus possible to prepare 2,4,6-trichlorophenol in this fashion by the chlorination of 2-chlorophenol with gaseous chlorine in the presence of an amine, which will first catalyze the chlorination of the 2-chlorophenol to 2,6-dichlorophenol and then the chlorination of the latter into 2,4,6-trichlorophenol.

It is also possible according to this invention to chlorinate a 2,6-dichlorophenol prepared by the chlorination of phenol using gaseous chlorine, again in the presence of an amine as described above.

The process of the invention is also applicable to the crude mixtures of chlorination of phenol, which contain 2,6-dichlorophenol as well as 2,4-dichlorophenol, orthochlorophenol and possibly minor amounts of parachlorophenol and phenol.

When applied to such industrial mixtures, the process of the invention enables 2,4,6-trichlorophenol to be produced almost exclusively and in excellent yield. In addition, 2,4,5-trichlorophenol, which is an undesirable compound, is virtualy absent.

The conditions described for the chlorination of the phenolic compounds of formula (I), and more especially of 2,6-dichlorophenol, apply to the chlorination of phenol and/or 2-chlorophenol, or of the crude industrial mixtures of chlorination of phenol mentioned above.

In order to further illustrate the present invention and the advantages thereof, the following specific examples are given, it being understood that same are intended only as illustrative and in nowise limitative.

EXAMPLE 1

A 200-cm$_3$ glass reactor equipped with a stirrer, a dipping tube permitting the introduction of gaseous chlorine and a thermometer, and surmounted by a condenser, was charged with:
  (i) 2,6-dichlorophenol: 32.6 g (0.2 mol);
  (ii) diisopropylamine: 0.33 g (equivalent to 1% by weight relative to the 2,6-dichlorophenyl).

The reaction mixture wa heated under stirring to 70° C. and gaseous chlorine was then introduced at a flow rate of 5 l/hr for 54 min, which represented a quantity of chlorine of 200 mmol.

Upon completion of the reaction, the apparatus was purged with a stream of nitrogen.

The reaction mass was analyzed by gas chromatography (GC) and by high performance liquid chromatography (HPLC).

The following results were obtained:
  (a) Degree of conversion (DC) of 2,6-dichlorophenol: 85.9%
  (b) Yield (YLD) of 2,4,6-trichlorophenol with respect to the 2,6-dichlorophenol converted: 95.9%
  (c) YLD of 2,3,4,6-tetrachlorophenol: 2.0%
  (d) Content of 2,4,5-trichlorophenol in the mixture: 0.0004%

COMPARATIVE TEST A

Example 1 was repeated, but without the diisopropylamine.

The following results were obtained:
  (a) DC of 2,6-dichlorophenol: 66.0%
  (b) YLD of 2,4,6-trichlorophenol: 76.0%
  (c) YLD of 2,3,4,6-tetrachlorophenol: 2.0%

EXAMPLE 2

The apparatus described in Example 1 was charged with:
  (i) ortho-chlorophenol: 32.1 g (0.25 mol);
  (ii) diisopropylamine: 0.3 g (equivalent to 1% by weight relative to the ortho-chlorophenol).

The reaction mixture was heated to 70° C. under stirring and chlorine was then introduced at a flow rate of 5 l/hr for 2 hr, 19 min, which corresponded to quantity of chlorine of 517 mmol.

The reaction mixture was analyzed by GC and HPLC.

The following results were obtained:
  (a) DC of ortho-chlorophenol: 100%
  (b) YLD of 2,4,6-trichlorophenol: 89.0%
  (c) YLD of 2,3,4,6-tetrachlorophenol: 3.0%
  (d) YLD of 2,4,4,6-tetrachloro-2,5-cyclohexadienone: 0.5%

EXAMPLE 3

The apparatus described in Eample 1 was charged with:
  (i) phenol: 32.9 g (0.35 mol);
  (ii) diisopropylamine: 0.33 g.

The reaction mixture was heated at 70° C. under stirring and chlorine was then introduced at a flow rate of 5 l/hr for 4 hr, 29 min, which corresponded to a quantity of chlorine of 1 mol.

The reaction mixture was analyzed by GC and HPLC.

The following results were obtained:
  (a) DC of phenol: 100%
  (b) YLD of 2,4,6-trichlorophenol: 91.8%
  (c) YLD of 2,6-dichlorophenol: 1.1%
  (d) YLD of 2,3,4,6-tetrachlorophenol: 1.6%
  (e) YLD of 2,4,4,6-tetrachloro-2,5-cyclohexadienone: 2.5%

EXAMPLE 4

The apparatus described in Example 1 was charged with:
(i) 2,6-dichlorophenol: 32.6 g (0.20 mol);
(ii) diisopropylamine: 0.03 g (equivalent to 0.1% by weight relative to the 2,6-dichlorophenol).

The reaction mixture was heated to 70° C. under stirring and chlorine was then introduced at a flow rate of 5 l/hr for 53 min, which corresponded to a quantity of chlorine of 0.2 mol.

The reaction mixture was analyzed by GC and HPLC.

The following results were obtained:
(a) DC of 2,6-dichlorophenol: 71.5%
(b) YLD of 2,4,6-trichlorophenol: 92.5%
(c) YLD of 2,3,4,6-tetrachlorophenol: 1.1%

EXAMPLE 5

The apparatus described in Example 1 was charged with 40 g of a crude industrial mixture of chlorophenols having the following composition by weight:
(i) ortho-chlorophenol: 0.22% (0.7 mmol);
(ii) 2,6-dichlorophenol: 23.63% (56 mmol);
(iii) 2,4-dichlorophenol: 42.32% (103.8 mmol);
(iv) 2,4,6-trichlorophenol: 26.3% (53.2 mmol);
(v) para-chlorophenol: 1.35% (4.2 mmol);
(vi) 2,4,5-trichlorophenol: 0.0822%.

After the mixture had been heated under stirring to 70° C., 188.75 mmol of chlorine, equivalent to a 10% excess with respect to the theoretical quantity needed for converting the chlorophenols completely to 2,4,6-trichlorophenol, was added over the course of 1 hour.

After the reactor had been purged with nitrogen, the final reaction mixture (96.2 g) was analyzed by GC and HPLC.

This mixture contained approximately 88% of 2,4,6-trichlorophenol, which corresponded to an approximately 98% yield with respect to the entire group of chlorophenols introduced.

The content of 2,4,5-trichlorophenol was approximately 0.0004%.

EXAMPLE 6

A 1,000-cm³ reactor equipped as described in Example 1 was charged with:
(i) 2,6-dichlorophenol: 32.6 g (0.2 mol);
(ii) tetrachloroethylene: 612 g;
(iii) diisopropylamine: 6.45 g (equivalent to 1% by weight relative to the reaction mixture).

The reaction mixture was heated under stirring to 70° C. and 4.48 liters of chlorine (0.2 mol) were introduced at this temperature over the course of 54 min.

When the reaction was complete, the apparatus was purged with nitrogen. The reaction mixture was analyzed by GC and HPLC after evaporation of the solvent.

The following results were obtained.
(a) DC of 2,6-dichlorophenol: 64%
(b) YLD of 2,4,6-trichlorophenol: 79%
(c) YLD of 2,3,4,6-tetrachlorophenol: 4%

COMPARATIVE TEST B

A 500-cm³ reactor equipped as described in Example 1, was charged with:
(i) 2,6-dichlorophenol: 24.45 g (0.15 mol);
(ii) tetrachloroethylene: 254 g.

The reaction mixture was heated under stirring to 70° C. and 3.36 liters of chlorine (0.15 mol) were introduced at this temperature over the course of 40 min.

When the reaction was complete, the apparatus was purged with nitrogen. The reaction mixture was analyzed by GC and HPLC after evaporation of the solvent.

The following results were obtained:
(a) DC of 2,6-dichlorophenol: 3%
(b) YLD of 2,4,6-trichlorophenol: 90%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a chlorophenol, comprising reacting a phenolic compound having the general formula (I):

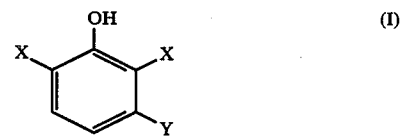

in which the symbols X, which may be identical or different, are each a chlorine atom, a bromine atom, a methyl or ethyl group, a methoxy or ethoxy group, an acetoxy group, an $NO_2$ group, or an acylamino group having 1 to 4 carbon atoms; and the symbol Y is a hydrogen atom, a methyl or ethyl group, or a methoxy or ethoxy group, with gaseous chlorine in the presence of a catalytically effective amount of a primary, secondary or tertiary amine.

2. The process as defined by claim 1, comprising carrying out the reaction in the molten state.

3. The process as defined by claim 1, comprising carrying out the reaction in a solvent medium.

4. The process as defined by claim 3, said solvent medium comprising an aliphatic ether, an aliphatic hydrocarbon, a chlorinated aliphatic hydrocarbon, a chlorobenzene or a bromobenzene.

5. The process as defined by claim 1, said amine catalyst having the general formula (II):

in which $R_1$, $R_2$ and $R_3$, which may be identical or different, are each a linear alkyl radical having from 1 to 12 carbon atoms, a secondary alkyl radical having from 3 to 12 carbon atoms or a tertiary alkyl radical having from 4 to 12 carbon atoms, with the proviso that such alkyl radicals may contain one or two —O—other groups or hydroxyl, amine, carboxylic acid, carboxylic acid ester, amide or imine groups; a phenyl radical, a cyclohexyl radical, a cycloheptyl radical or a cyclopentyl radical; a phenylalkyl, cyclohexylalkyl, cycloheptylalkyl or cyclopentylalkyl radical, the alkyl moiety of which contains from 1 to 4 carbon atoms; or a hydrogen atom; with the further provisos that:

R₁ may be an NH₂ group;

R₂ and R₃ may form, together with the nitrogen atom from which they depend a saturated heterocycle or a heterocycle containing at least one double bond, or a saturated heterocycle or a heterocycle containing at least one double bond substituted with at least one alkyl group having from 1 to 4 carbon atoms;

R₂ and R₃ or R₁, R2 and R3 may form, together with the nitrogen atom from which they depend and with at least one other nitrogen, oxygen, sulfur atom, or combination thereof, a saturated or unsaturated heterocycle, or a saturated or unsaturated heterocycle substituted with at least one alkyl group having from 1 to 4 carbon atoms;

R₁, R₂ and R3 may form, together and with the nitrogen atom from which they depend, an unsaturated heterocycle or an unsaturated heterocycle substituted with one or two methyl or ethyl groups; and R₂ and R₃ or R₁, R₂ and R3 may form, together with the nitrogen atom from which they depend or the nitrogen atom from which they depend with at least one other nitrogen, oxygen, sulfur atom or combination thereof, a saturated or unsaturated polycyclic compound or a saturated or unsaturated polycyclic compound substituted with at least one alkyl group having 1 to 4 carbons atoms.

6. The process as defined by claim 5, wherein the amount of said amine present constitute from 0.005% to 25% by weight of the phenolic compound (I).

7. The process as defined by claim 1, said amine catalyst having the general formula (III):

in which R₂ or R₃ may be a hydrogen atom; and R₂ and R₃, which may be identical or different, are each a linear alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical; with the provisos that:

R₂ and R₃ may form, together with the nitrogen atom from which they depend and with at least one other of a nitrogen or oxygen atom, a saturated heterocycle or a heterocycle containing at least one olefinic double bond; and at least one of R₂ and R₃ may contain at least one amine, hydroxyl or carboxylic acid ester groups.

8. The process as defined by claim 7, wherein said amine catalyst having the general formula (III), at least one of R₂ and R₃ is a secondary alkyl radical having from 3 to 10 carbon atoms.

9. The process as defined by claim 8, wherein at least one of R₂ and R₃ is an isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl, 5-decyl, cyclohexyl or cyclopentyl radical.

10. The process as defined by claim 7, wherein said amine catalyst having the general formula (III), R₂ and R₃ together form, with the nitrogen atom from which they depend, a 5- or 6-membered heterocycle or a 5- or 6-membered heterocycle containing another nitrogen atom or an oxygen atom.

11. The process as defined by claim 7, wherein said amine catalyst having the general formula (III) comprises n-propylamine, isopropylamine, n-butylamine, isobutylamine, tert-butylamine, n-pentylamine, 2-methylpentylamine, 3-methylpentylamine, 2-ethylhexylamine, laurylamine, cyclohexylamine, cyclopentylamine, benzylamine, glycine ethyl ester, ethanolamine, diisopropylamine, diisobutylamine, dicyclohexylamine, morpholine or imidazole.

12. The process as defined by claim 1, said phenolic compound (I) comprising 2,6-dichlorophenol, 2,6-dimethoxyphenol, 2-chloro-6-methoxyphenol, 2-chloro-6-methylphenol, 2,6-dichloro-3-methylphenol, 2,6-dichloro-3-methoxyphenol, 2-bromo-6-methoxyphenol, 2-chloro-6-nitrophenol or 2-chloro-6-acetamidophenol.

13. The process as defined by claim 12, said phenolic compound (I) comprising 2,6-dichlorophenol.

14. The process as defined by claim 1, carried out at a temperature ranging from the melting point of the phenolic compound (I) to 120° C.

15. The process as defined by claim 13, said 2,6-dichlorophenol having been prepared by reacting 2-chlorophenol with gaseous chlorine in the presence of a catalytically effective amount of a primary, secondary or tertiary amine.

16. The process as defined by claim 13, said 2,6-dichlorophenol having been prepared by reacting phenol with gaseous chlorine in the presence of a catalytically effective amount of a primary, secondary or tertiary amine.

17. The process as defined by claim 1, said phenolic compound (I) comprising crude admixture of 2,6-dichlorophenol, 2,4-dichlorophenol, ortho-chlorophenol, or crude admixture of 2,6-dichlorophenol, 2,4-dichlorophenol, ortho-chlorophenol and minor amounts of parachlorophenol and phenol.

18. The process as defined by claim 1, for the preparation of 2,4,6-trichlorophenol.

* * * * *